United States Patent
Ramakrishna et al.

(10) Patent No.: US 10,393,709 B2
(45) Date of Patent: Aug. 27, 2019

(54) HOISTING AND HOLDING SYSTEM FOR CHROMATOGRAPHY COLUMN

(71) Applicant: GE Healthcare Bio-Sciences AB, Uppsala (SE)

(72) Inventors: Manoj Ramakrishna, Bangalore (IN); Kishore Chengalvarayan, Bangalore (IN); Nikhil Kamble, Bangalore (IN)

(73) Assignee: GE HEALTHCARE BIO-SCIENCES AB, Uppsala (SE)

(*) Notice: Subject to any disclaimer, the term of this patent is extended or adjusted under 35 U.S.C. 154(b) by 273 days.

(21) Appl. No.: 15/303,095

(22) PCT Filed: Mar. 30, 2015

(86) PCT No.: PCT/EP2015/056863
§ 371 (c)(1),
(2) Date: Oct. 10, 2016

(87) PCT Pub. No.: WO2015/155045
PCT Pub. Date: Oct. 15, 2015

(65) Prior Publication Data
US 2017/0030872 A1   Feb. 2, 2017

(30) Foreign Application Priority Data

Apr. 12, 2014  (IN) .......................... 1029/DEL/2014

(51) Int. Cl.
*G01N 30/60* (2006.01)
*B01D 15/22* (2006.01)
*G01N 30/02* (2006.01)

(52) U.S. Cl.
CPC ......... *G01N 30/6047* (2013.01); *B01D 15/22* (2013.01); *G01N 30/6021* (2013.01); *G01N 2030/027* (2013.01)

(58) Field of Classification Search
CPC .................. G01N 30/6047; B01D 15/22
See application file for complete search history.

(56) References Cited

U.S. PATENT DOCUMENTS 7,238,282 B2   7/2007   Perreault et al.
7,452,464 B2   11/2008  Uselius et al.
(Continued)

FOREIGN PATENT DOCUMENTS

CN   101068609 A   11/2007
JP    08012292 A    1/1996
(Continued)

OTHER PUBLICATIONS

Office Action for Chinese Patent Appl. No. 201580031123.4, filed Mar. 30, 2015, 19 pages, dated Mar. 15, 2018.
(Continued)

*Primary Examiner* — Justin Seo
*Assistant Examiner* — David Z Huang
(74) *Attorney, Agent, or Firm* — Wood IP LLC

(57) ABSTRACT

A holding system for holding and hoisting a chromatography column of one or more chromatography columns is disclosed. The holding system includes an upright member and a plurality of holding members movably arranged along the upright member. A first supporting member is positioned at an end portion of the chromatography column, wherein a holding member of the plurality of holding members is configured to be engaged to the first supporting member. A second supporting member is positioned at another end portion of the chromatography column. A holding member of the plurality of holding members is configured to be engaged to the second supporting member. One or more hoist assisting members may be also present. A hoist assisting member is operatively connected to the holding member engaged to the first supporting member. The hoist assisting member is operable to move the holding member connected to the first supporting member for hoisting the chromatography column.

21 Claims, 9 Drawing Sheets

(56) References Cited

U.S. PATENT DOCUMENTS

| | | | |
|---|---|---|---|
| 7,708,891 B2 | 5/2010 | Davis et al. | |
| 8,246,833 B2 | 8/2012 | Eriksson et al. | |
| 8,585,894 B1 | 11/2013 | Uselius | |
| 2008/0290016 A1 | 11/2008 | Bailey et al. | |
| 2013/0087491 A1* | 4/2013 | Ramakrishna | B01D 15/10 |
| | | | 210/232 |

FOREIGN PATENT DOCUMENTS

| | | |
|---|---|---|
| JP | 110130384 A | 5/1999 |
| JP | 2000026090 A | 1/2000 |
| JP | 2005098734 A | 4/2005 |
| JP | 2017083471 A | 5/2017 |
| WO | 2006/048058 A1 | 5/2006 |
| WO | 2011/073067 A1 | 6/2011 |
| WO | 2013/191629 A1 | 12/2013 |

OTHER PUBLICATIONS

International Search Report and Written Opinion regarding International Application No. PCT/EP2015/056863, dated Jun. 16, 2015, 14 pages.

Japan Notice of Preliminary Rejection for Japanese Patent Application No. 2016-561678, dated Jan. 15, 2019, 7 pages.

* cited by examiner

HOISTING AND HOLDING SYSTEM FOR CHROMATOGRAPHY COLUMN

CROSS-REFERENCE TO RELATED APPLICATIONS

This application is a filing under 35 U.S.C. 371 of international application number PCT/EP2015/056863, filed Mar. 30, 2015, which claims priority to IN application number 1029/DEL/2014, filed Apr. 12, 2014, the entire disclosures of each of which are hereby incorporated by reference.

FIELD OF THE INVENTION

The subject matter disclosed herein relates to holding and hoisting chromatography columns and more particularly to a holding and hoisting system for holding and hoisting a process scale chromatography column used in a chromatography system. The chromatography system is used for separation of protein samples.

BACKGROUND OF THE INVENTION

Chromatography columns may be used in industrial processes to purify process liquids and separate substances of interest from process liquids. Typical examples include large-scale preparative purification of fine chemicals and pharmaceuticals, together with biological products.

Process-scale chromatography columns typically comprise a hollow, axially vertical tubular housing including a liquid inlet at the upper end and through which the buffer and substances to be separated are dispensed to the media bed located within the cavity of the tube, and a liquid collecting system at the lower end for collecting substances and buffer. The particulate chromatographic media or bed through which the buffer fluid and/or substances to be separated and purified percolates is located between the liquid inlet and collecting system.

An adapter assembly is typically affixed to the upper end of the tubular housing and a base assembly to the lower end where it is bolted to the bottom flanges. Each of these assemblies typically comprises a strong backing plate and a distributor which further supports a bed support. A bed support is a layer of mesh, filter, sinter, screen or other fluid-permeable media-retaining material which permits process liquid flow into and out of the chromatography bed space or cavity while retaining the bed of particulate medium. To provide adjustability and control of the bed height and bed compression, the adapter assembly is typically made in the form of a piston or sliding adapter in the column tube interior. After the column is charged with bed media, typically through a nozzle, the adapter may be forced toward the bottom of the tube to compress or pressurize the media bed. Generally, the base assembly is a fixed structure which is bolted against the bottom flange of the column tube but, in some instances, may also be in the form of a movably slidable piston or adapter. The backing plate of the base assembly generally acts as a support for the column, being itself supported on legs or some other stand arrangement which allows clearance for outlet pipe work projecting beneath the base assembly.

When such a column requires maintenance or cleaning of internal components, such as the valves, seals, meshes/screens, distribution systems etc., heavy lifting gear such as a crane or hoist is necessary to lift the upper end/adapter assembly away from the column tube and the column tube away from the lower end/base assembly as these assemblies can weigh in excess of three tons. The use of heavy overhead lifting equipment to disassemble the column in order to carry out internal maintenance is not desirable. Operator safety is obviously a concern when heavy equipment is lifted overhead and technicians exposed below. Furthermore, alignment structures are required to keep the column and its base/adapter assemblies axially aligned as they are separated from each other, to avoid damage to the precision components such as mesh, distributor and column tube.

The presence of such alignment and lifting structures imposes significant obstructions around the tube and need to be carefully laid out to provide sufficient clearance at some point of the circumference for insertion/removal of the internal components. Furthermore, the requirement to use heavy lifting equipment imposes constraints on housing such columns, sufficient overhead space and support being required to accommodate hoists or cranes. As many chromatography columns are now run in "clean" environments under GMP, to avoid microbiological contamination, where it is extremely difficult to accommodate overhead equipment, the requirement of moving the column to another room for disassembly and maintenance is problematic. This problem is exacerbated by the need to clean and verify the column before returning it for use to the clean environment. The presence of hoists or cranes in GMP facilities used for biopharmaceutical manufacturing is thus highly undesirable for the above mentioned reasons, together with the fact that these machines shed particulate matter, in the form of dirt, during their operation and maintenance.

Accordingly, a need exists to improve the maintenance methods and system for holding and hoisting the chromatography columns which are safer and easier for operators to use and which do not expose them to a suspended or supported load, thereby reducing the risk of operator error and injury.

SUMMARY OF THE INVENTION

The object of the invention is to provide an improved holding system for holding and hoisting a chromatography column of one or more chromatography columns, which overcomes one or more drawbacks of the prior art. This is achieved by a chromatography system including a holding system for holding and hoisting a chromatography column as defined in the independent claim.

One advantage with the disclosed is that a chromatography system including a holding system for holding and hoisting a chromatography column of one or more chromatography columns may not require any complex hoist unit which can damage the expensive column components while lifting and positioning the heavy components.

Hoist and holding system can be provided as an accessory to complement a wide variety of process columns that exists in market. User will need single accessory for maintenance of many columns thereby overall cost of ownership will be reduced.

In an embodiment a holding system for holding and hoisting a chromatography column of one or more chromatography columns is disclosed. The holding system includes an upright member and a plurality of holding members movably arranged along the upright member. A first supporting member is positioned at an end portion of the chromatography column, wherein a holding member of the plurality of holding members is configured to be engaged to the first supporting member. A second supporting member is positioned at another end portion of the chromatography column. A holding member of the plurality of holding members is configured to be engaged to the second supporting member. One or more hoist assisting members may be also present. A hoist assisting member is operatively connected to the holding member engaged to the first supporting member. The hoist assisting member is operable to move the holding member connected to the first supporting member for hoisting the chromatography column.

In another embodiment a chromatography system includes a chromatography column, a chromatography stand onto which the chromatography column is positioned and an adapter movable in the chromatography column, wherein the chromatography system includes an upright member, a plurality of holding members movably arranged along the upright member; a first supporting member positioned at an end portion of the chromatography column, wherein a holding member of the plurality of holding members is configured to be engaged to the first supporting member, the adapter is operatively connected to the first supporting member for moving in the chromatography column; a second supporting member positioned at another end portion of the chromatography column, wherein the second supporting member is comprised in the chromatography stand, wherein a holding member of the plurality of holding members is configured to be engaged to the second supporting member; and one or more hoist assisting members, wherein a hoist assisting member is operatively connected to the holding member engaged to the first supporting member, the hoist assisting member is operable to move the holding member connected to the first supporting member for hoisting at least one of the chromatography column and the adapter.

In an embodiment a method of holding and hoisting a chromatography column using a holding system is disclosed. The method comprises positioning a first supporting member at an end portion of the chromatography column, wherein the upright member have a plurality of holding members movably arranged along the upright member, wherein a holding member of the plurality of holding members is configured to be engaged to the first supporting member; positioning a second supporting member at another end portion of the chromatography column, wherein a holding member of the plurality of holding members is configured to be engaged to the second supporting member; and operating a hoist assisting member operatively connected to the holding member engaged to the first supporting member, wherein upon operation of the hoist assisting member the holding member connected to the first supporting member moves for hoisting the chromatography column.

A more complete understanding of the present invention, as well as further features and advantages thereof, will be obtained by reference to the following detailed description and drawings.

DETAILED DESCRIPTION OF THE INVENTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical and other changes may be made without departing from the scope of the embodiments. The following detailed description is, therefore, not to be taken as limiting the scope of the invention.

As discussed in detail below, embodiments of the invention including a holding system for holding and hoisting a chromatography column of one or more chromatography columns is disclosed. The holding system includes an upright member and a plurality of holding members movably arranged along the upright member. A first supporting member is positioned at an end portion of the chromatography column, wherein a holding member of the plurality of holding members is configured to be engaged to the first supporting member. A second supporting member is positioned at another end portion of the chromatography column. A holding member of the plurality of holding members is configured to be engaged to the second supporting member. One or more hoist assisting members may be also present. A hoist assisting member is operatively connected to the holding member engaged to the first supporting member. The hoist assisting member is operable to move the holding member connected to the first supporting member for hoisting the chromatography column.

Figure 1:
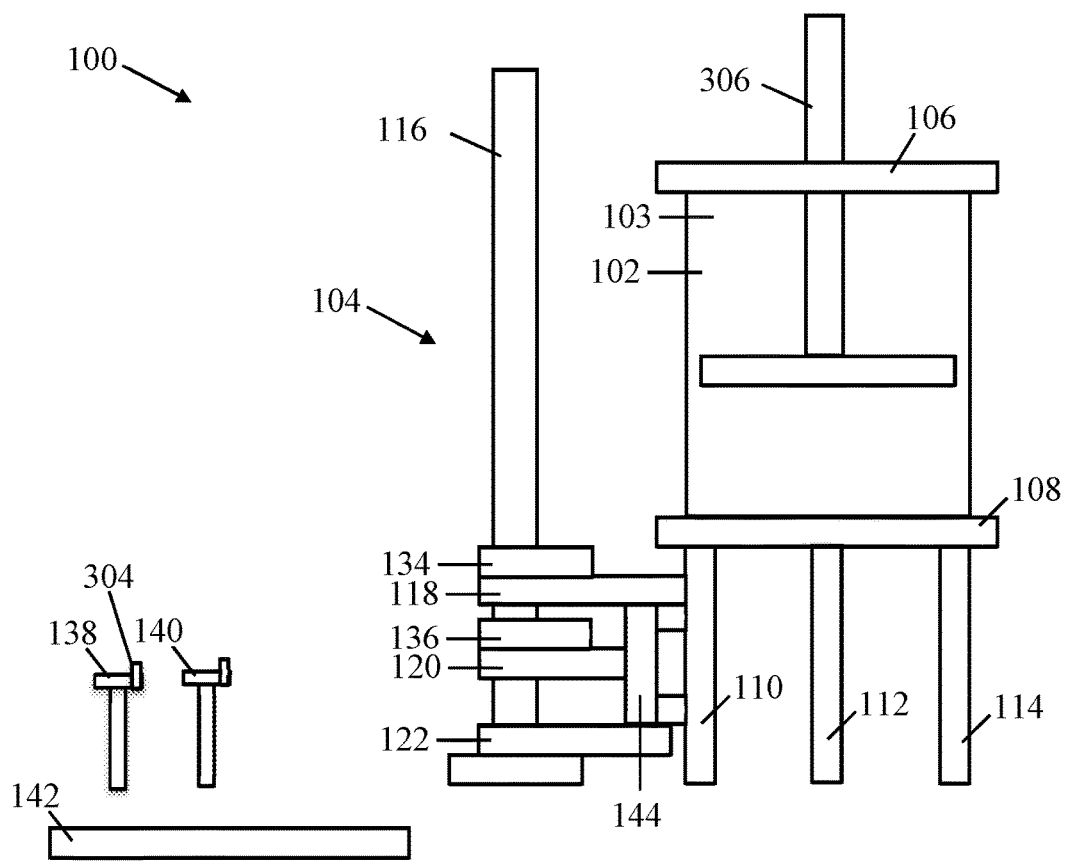
FIG. 1 is a side view of a holding system for holding and hoisting an chromatography column of one or more chromatography columns in a disassembled configuration in accordance to an embodiment.
Figure 2:
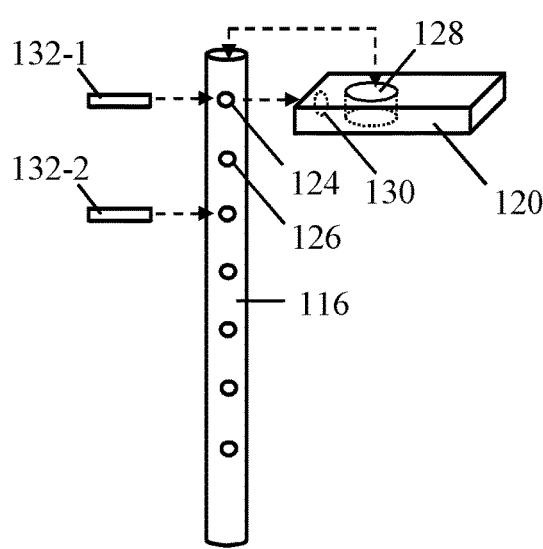
FIG. 2 is a schematic illustration of a holding system in an exploded configuration in accordance to an embodiment.

FIG. 1 is a side view of a holding system 100 for holding and hoisting a chromatography column of one or more chromatography columns in accordance with an embodiment. The holding system 100 is shown in an unassembled configuration. A chromatography column 102 is held by the holding system 100. The chromatography column 102 may be placed on a chromatography stand 104 (hereinafter referred to as a stand 104), and have a first supporting member 106 positioned at an end portion 103 of the chromatography column 102. The stand 104 includes a second supporting member 108 with multiple legs such as legs 110, 112 and 114. The holding system 100 includes an upright member 116 and a plurality of holding members such as a holding member 118, a holding member 120 and a holding member 122 movably arranged along the upright member 116. The holding members can be arranged at different positions of the upright member 116 based on needs. The upright member 116 has multiple holes for enabling a fastening member to pass through the upright member 116 and finally into a slot in a holding member to position it on the upright member 116. As shown in FIG. 2, the upright member 116 may have multiple holes such as holes 124 and 126. The holes 124 and 126 may pass through entire diameter of the upright member 116. In another embodiment the holes 124 and 126 may pass only till half-way along the diameter of the upright member 116. The holding member 120 is arranged along the upright member 116 when the upright member 116 passes through a slot 128. The slot 128 may extend along its height of the holding member 120. The holding member 120 also have a locking slot 130 at one end portion that enables a locking unit 132-1 to pass through the hole 124 and the locking slot 130 to lock the holding member 120 at the position near the hole 124 or overlapping the hole 124. Another locking unit 132-2 may be also present in the holding system 100. The holes 124 and 126 are shown to be circular in configuration however these holes can have different configurations such as square, rectangular, triangular and any parallelogram. Based on the configuration of these holes, a locking slot in a holding member and a locking member may have complementary shape and configuration. In another embodiment the holes may have its internal surface in a threaded configuration so that the locking unit 132 may be a screw like member that can pass through the hole. Further it may be appreciated that the disclosed arrangement for arranging the holding members along the upright member is in accordance to an exemplary embodiment and hence it may be envisioned that other constructional arrangements of position locking mechanisms may be possible for arranging the holding members along the upright member. These holding members may have different sizes and shapes based on different requirements.

The holding system 100 also includes multiple plate members for instance a plate member 134 and a plate member 136. The plate member 134 is operatively connected to the holding member 118 using a hoist assisting member 138 and the plate member 136 is operatively connected to the holding member 120 using a hoist assisting member 140. This is described in detail in conjunction with FIG. 3. The hoist assisting members 138 and 140 are shown in a disassembled configuration in FIG. 1.

In order to hold the chromatography column 102 in a correct position the holding system 100 may be provided with a clasping member 142 that can be connected to a holding member. The clasping member 142 may be wound around the chromatography column 102. The clasping member 142 may be a belt like member that can be wound around the chromatography column 102 and disengageably engaged to the holding member such as the holding member 120. The holding member 120 includes a gripping unit 144. The gripping unit 144 enables the holding member 120 to be held securely along with the holding force of the clasping member 142. The holding member 120 along with the gripping unit 144 may have a T-shaped configuration according to an embodiment.

Figure 3:
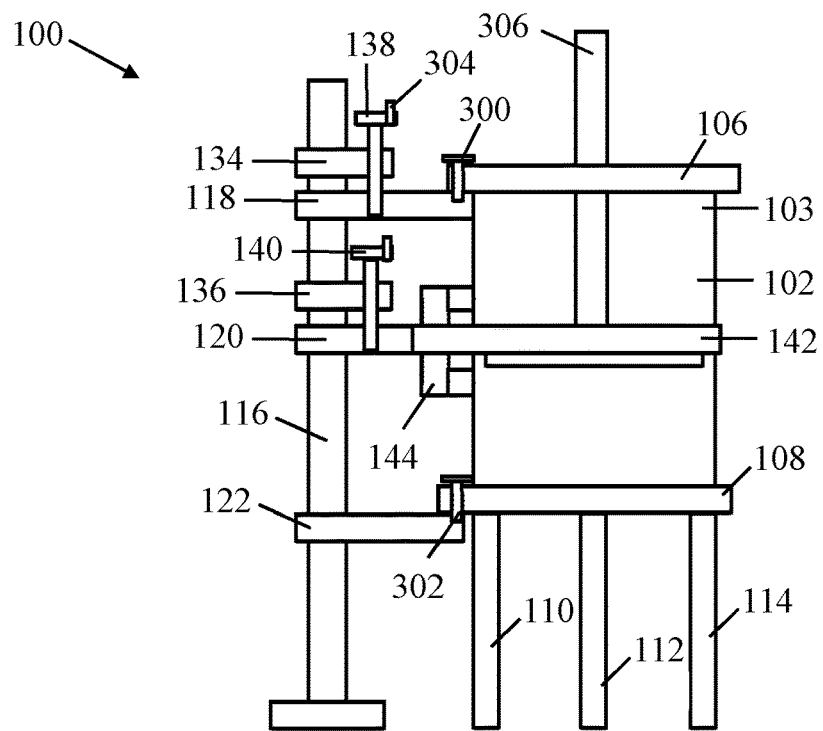
FIG. 3 is a schematic illustration of the holding system in an assembled configuration holding a chromatography column in accordance to an embodiment.

FIG. 3 illustrates the holding system 100 in an assembled configuration holding the chromatography column 102 in accordance to an embodiment. In the assembled configuration, the holding member 118 is connected to the first supporting member 106 using a fastening member 300 according to an embodiment. The fastening member 300 may be a screw member, a hook member, a nut and bolt unit, a clipping member and so on. In another embodiment the holding member 118 may be connected to the first supporting member 106 using any other connecting mechanisms. Similarly the holding member 122 is connected to the second supporting member 108 using a fastening member 302. The fastening member 302 may be similar to the fastening member 300 and accordingly this may be a screw member, a hook member, a nut and bolt unit, a clipping member and so on.

The plate member 134 is connected to the first supporting member 106 using the hoist assisting member 138. The hoist assisting member 138 may have threads along its length similar to a screw along with a handle 304. The handle 304 can be used by a user to rotate the hoist assisting member 138 engaging the plate member 134 and the first supporting member 106. The first supporting member 106 holds the adapter 306 as shown in FIG. 3. The hoist assisting member 138 can be used to change the position of the first supporting member 106 for instance lifting the first supporting member 106. Further the plate member 136 is connected to the holding member 120 positioned substantially at a mid-portion of the chromatography column 102 using the hoist assisting member 140. The clasping member 142 is engaged with the holding member 120 and wound around the chromatography column 102 as shown in FIG. 3. Thus all the three holding members, clasping member 142 and the gripping unit 144 of the holding member 120 enables the chromatography column to be securely placed in position on the stand 104.

Figure 4:
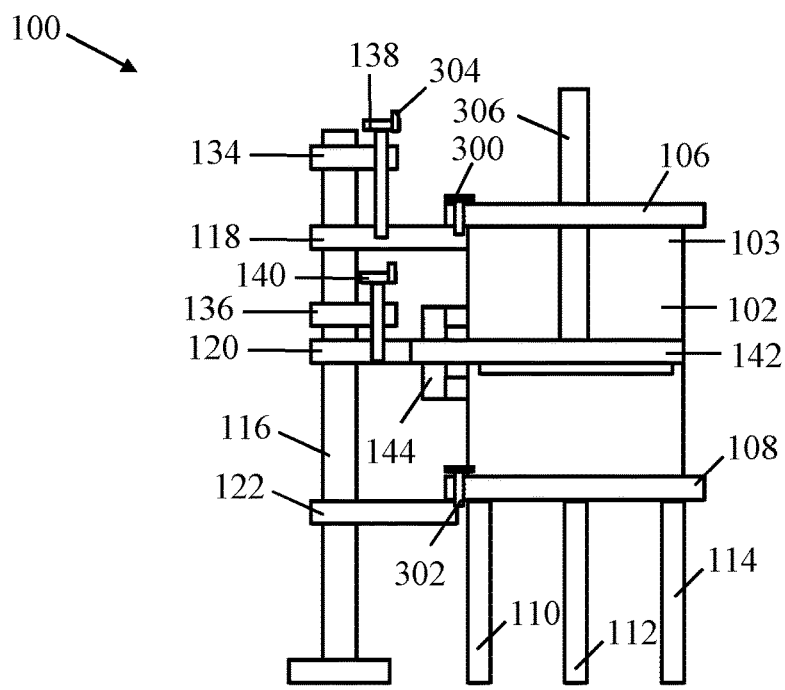
FIG. 4 is a schematic illustration showing the operation of a hoist assisting member in a holding system in accordance to an embodiment.
Figure 5:
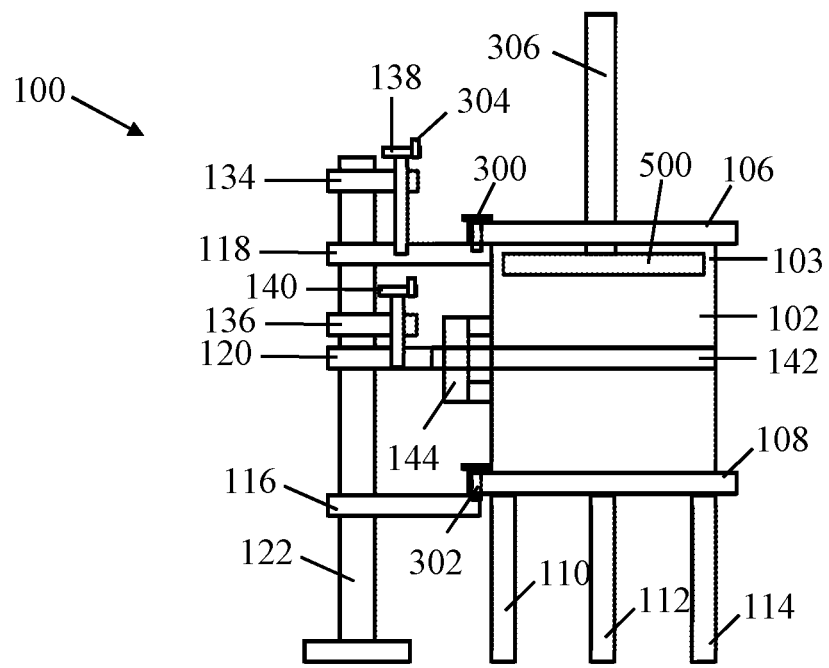
FIG. 5 is a schematic illustration showing the operation of the hoist assisting member in a holding system for lifting an adapter from a chromatography column in accordance to an embodiment.
Figure 6:
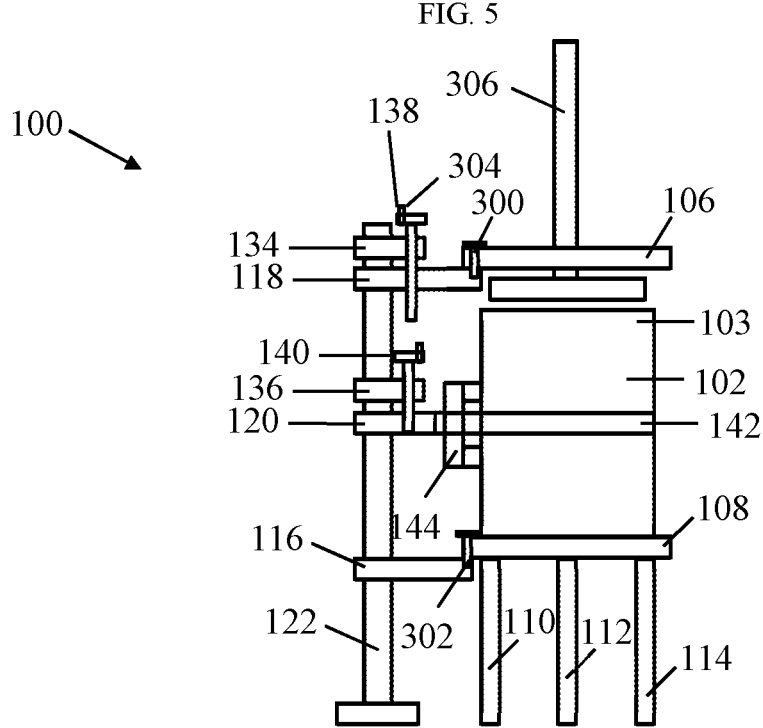
FIG. 6 is schematic illustrations showing the adapter lifted from the chromatography column in accordance to an embodiment.

The adapter 306 may need to be removed after usage from the chromatography column 102. For this the first supporting member 106 along with the adapter 306 needs to be lifted. FIG. 4 illustrates the holding system 100 having the hoist assisting member 138 adjusted for lifting the adapter 306 in accordance with an embodiment. The hoist assisting member 138 may be operated to loosen from the holding member 118. Thus the hoist assisting member 138 as shown extends out of the holding member 118 as illustrated in FIG. 4. The plate member 134 connected to the hoist assisting member 138 may be also moved up to be positioned at a higher slot on the upright member 116. For example, the plate member 134 may be moved to be initially positioned at the hole 124 as shown in FIG. 3. Then the plate member 134 may be moved up to be positioned aligning to the hole 126. The adapter 306 is pulled up so that its base portion 500 moves closer to the first supporting member 106 as illustrated in FIG. 5. The adapter 306 is pulled up by a user or a technician. The adapter 306 may be moveably engaged with the first supporting member 106 such that it can be moved up and down. Thereafter the hoist assisting member 138 is tightened to move the holding member 118 closer to the plate member 134. As a result the first supporting member 106 moves with respect to the plate member 134 (i.e. the first supporting member 106 moves closer to the plate member 134) thereby lifting the adapter 306 out of the chromatography column 102 as illustrated in FIG. 6 according to an embodiment. Once the adapter 306 is removed the chromatography column 102 can be cleaned. The adapter 306 can be removed manually now as this is completely out of the chromatography column 102.

Figure 7:
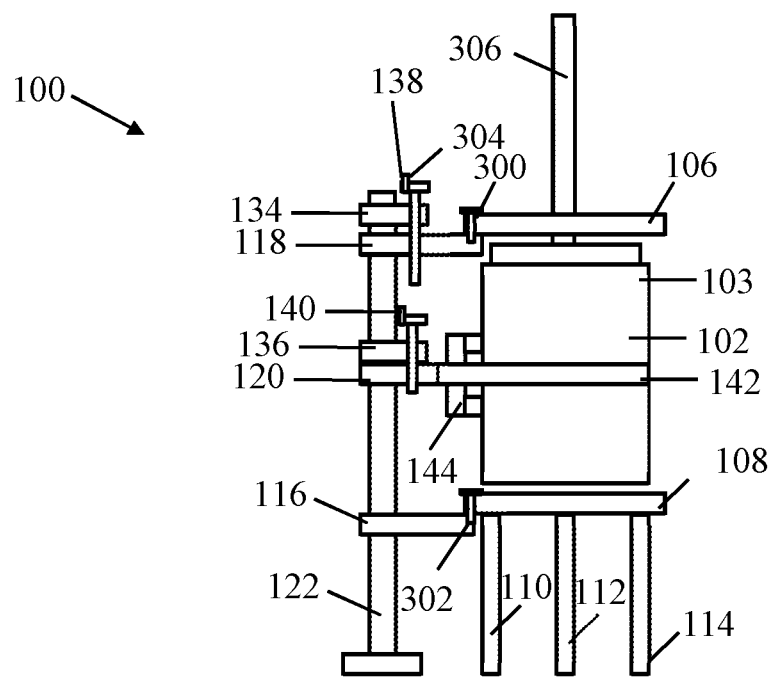
FIG. 7 is schematic illustration showing operation of a hoist assisting member for lifting the chromatography column from a stand in accordance to an embodiment.
Figure 8:
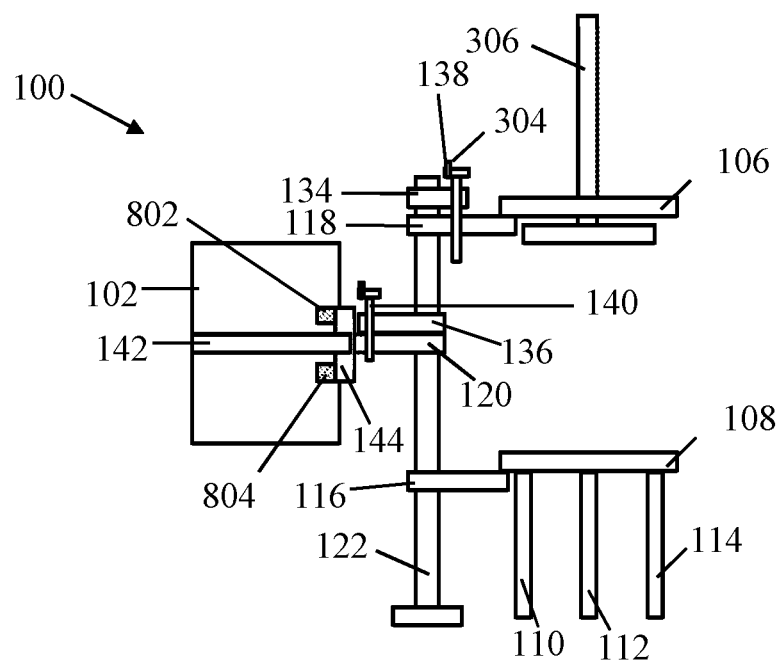
FIG. 8 is a schematic illustration of the chromatography column swinged away and positioned out from the stand in accordance to an embodiment.

FIG. 7 illustrates the holding system 100 having the adapter 306 in a lifted position according to an embodiment. The hoist assisting member 140 is operated (i.e. rotated) using its handle 700 for moving up the holding member 120 closer to the plate member 136. This is done so that additional strength in gripping or holding the chromatography column 102 is provided to the gripping unit 144 and the clasping member 142. The holding member 120 along with the clasping member 142 holding the chromatography column 102 can swing with respect to the upright member 116 for moving the chromatography column 102 away from the stand 104 as shown in FIG. 8 according to an embodiment. In this embodiment the holding member 120 may be rotated or swung after removing or disengaging a locking unit such as the locking unit 132 from a corresponding hole in the upright member 116. In other embodiments other position locking mechanisms may enable the holding member 120 to be positioned along the upright member 116. These position locking mechanisms may be adjusted so that the holding member 120 can loosen from a current position on the upright member 116 thereby enabling the holding member 120 to swing with respect to the upright member 116. Once the chromatography column 102 is swung away from the upright member 116 the column 102 can be removed by the technician and serviced or cleaned for performing the maintenance.

Further to securely hold the chromatography column 102, the holding member 120 is provided with one or more pads. Pads 800 and 802 are positioned between the gripping unit 144 and the chromatography column 102. The pads 800 and 802 come in contact with the surface of the chromatography column 102 when the clasping member 142 is wound around the column 102. The pads 800 and 802 render more grip onto the surface of the chromatography column 102. The pads 800 and 802 may be made of rubber material. The pads 800 and 802 may be composed of any other flexible materials known in the art. The flexible materials can provide sufficient amount of grip for holding any chromatography column when it is in contact and will not damage expensive column tube surface. The pads 800 and 802 may be fastened on to the surface of the gripping unit 144. In an embodiment the pads 800 and 802 may be stuck onto the gripping unit 144 using a binding material such as a glue material. In another embodiment the pads 800 and 802 may be arranged on the gripping unit 144 using one or more fastening members. The fastening members may include but are not limited to screws, nut and bolts, clips, pins and so on.

Figure 9:
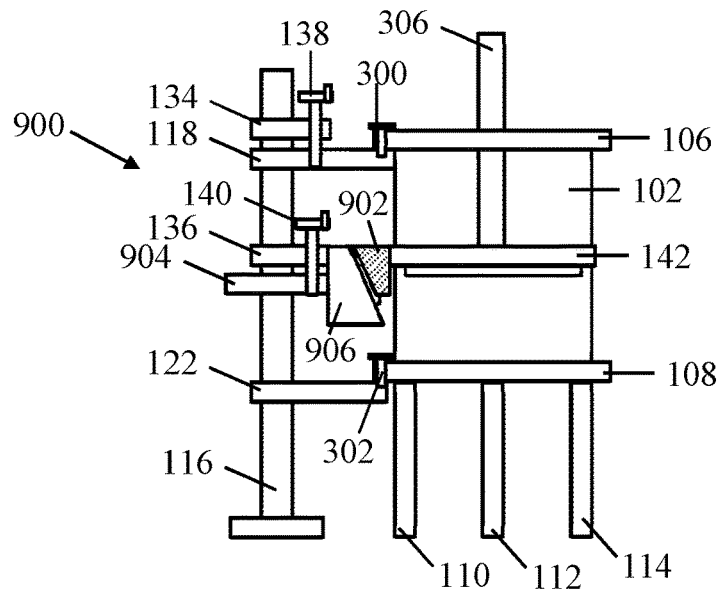
FIGS. 9 and 10 are schematic illustrations of a holding system including wedge shaped pads arranged in a holding member for holding the chromatography column in accordance to an embodiment.

FIG. 9 illustrates a holding system 900 including a pad 902 arranged proximal to a holding member 904 for holding the chromatography column 102 in accordance with an embodiment. The pad 902 may be a wedge shaped pad. The wedged shaped pad may be arranged on a gripping unit 906 of the holding member 904. The gripping unit 906 may also have a wedge shape so that it can match with the shape of the pad 902. The pad 902 may be fastened on to the surface of the gripping unit 906. In an embodiment the pad 902 may slide with the gripping unit 906 using a dove tail joint or any other similar arrangement. In another embodiment the pad 902 may be arranged on the gripping unit 906 using one or more fastening members. The fastening members may include but are not limited to screws, nut and bolts, clips, pins and so on.

Figure 10:
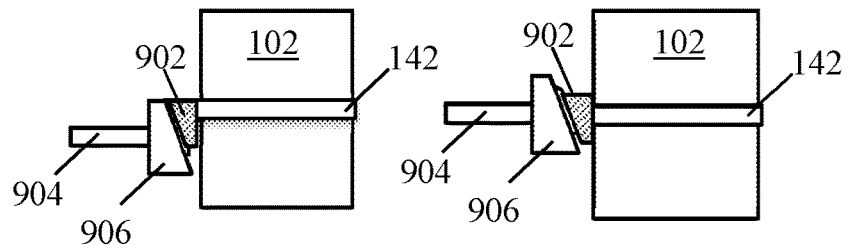

In an embodiment the gripping unit 906 may include a track unit 908 on which the pad 902 may be mounted as illustrated in FIG. 10. The pad 902 may move along the track unit 908. The track unit 908 may have locking mechanism that prevents the pad 902 from sliding out of the track unit 908. The pad moves along the track unit 908 for efficiently gripping the chromatography column 102 in place on the stand 104. The wedge shaped pad 902 and the tracking unit 908 prevents the chromatography column 102 from slipping out from its position. The wedge shaped pad helps in good way to take up vertical load component of the chromatography column 102

Figure 11:
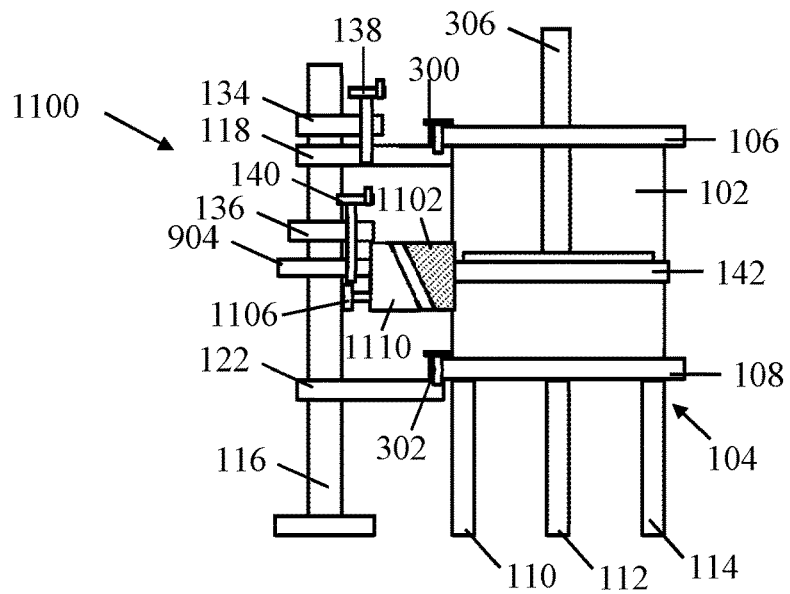
FIGS. 11 and 12 are schematic illustrations of a holding system including pads having suction mechanisms arranged in a holding member for holding the chromatography column in accordance to an embodiment.
Figure 12:
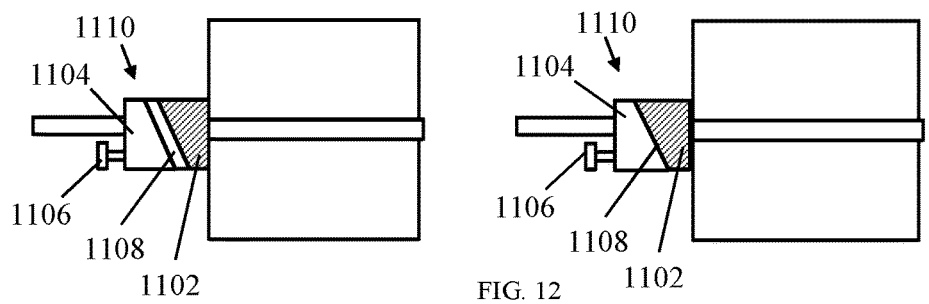

FIGS. 11 and 12 illustrate a holding system 1100 including a pad 1102 for holding the chromatography column 102 in accordance with another embodiment. The pad 1102 includes a suction unit 1104. The suction unit 1104 includes a suction pump 1106 which when operated produces the suction effect for gripping the chromatography column 102. The pad 1102 may be a wedge shaped pad. There is a gap 1108 visible (shown in FIG. 11 and FIG. 12) between the gripping unit 1110 and the pad 1102 when the suction pump 1106 is not engaged. The pad 1102 may be in contact with the surface of the chromatography column 102 and have the gap 1108 visible as shown in FIG. 12. Now if the chromatography column 102 needs to be held, the suction pump 1106 is operated to engage for producing the suction effect. This results in the pad 1102 pulling the chromatography column 102 or the pad 1102 moving closer to the chromatography column 102 to firmly hold the column. In this stage the gripping unit 1110 firmly touches the pad 1102 so that gap 1108 is no longer visible. The pad 1102 may include a hole (not shown in FIG. 11 and FIG. 12) that sucks the air between the pad 1102 and the surface of the chromatography column 102 for firmly holding it in response to operating the suction pump 1106. The suction pump 1106 may be operated by rotating it or by pulling and pushing operation. Even though an exemplary arrangement of a suction unit for operating the pads is described herein however it may be envisioned that other embodiments may include different arrangements for producing the suction effect for operating the pads to hold the chromatography column firmly.

Figure 13:
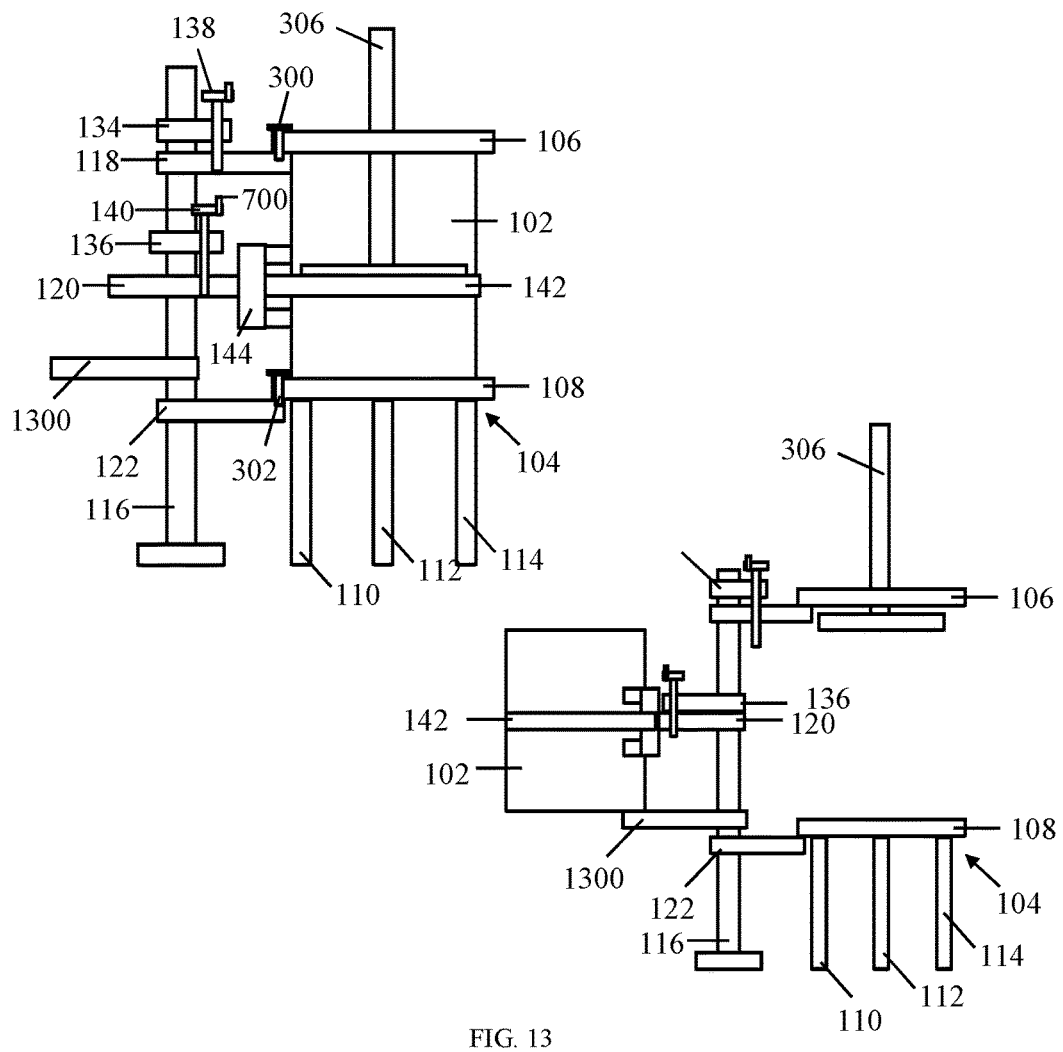
FIG. 13 is a schematic illustration of the chromatography column swung away and positioned out from the stand and rested on a supporting plate in accordance to yet another embodiment.

FIG. 13 illustrates the holding system 100 having the chromatography column 102 positioned by swinging away from the stand 104 according to another embodiment. The holding system 100 also includes another holding member 1300 which can act as support for the chromatography column 102 when it is moved away from the stand 104 by swinging the holding member 120. So once swung the chromatography column 102 moves out of the stand 104 and gets seated on the holding member 120. The swinging operation is done only once the adapter 306 is removed from the chromatography column 102 as described in conjunction with FIGS. 4, 5 and 6. At this position the clasping member 142 and the gripping unit 144 may be still holding the chromatography column 102 intact. Similarly, it may be noted that additional holding members can be arranged along the upright member 116 at different positions based on the requirements. The additional holding member 1300 (in the form of a support plate) will be used for resting the heavy column after swinging out.

Figure 14:
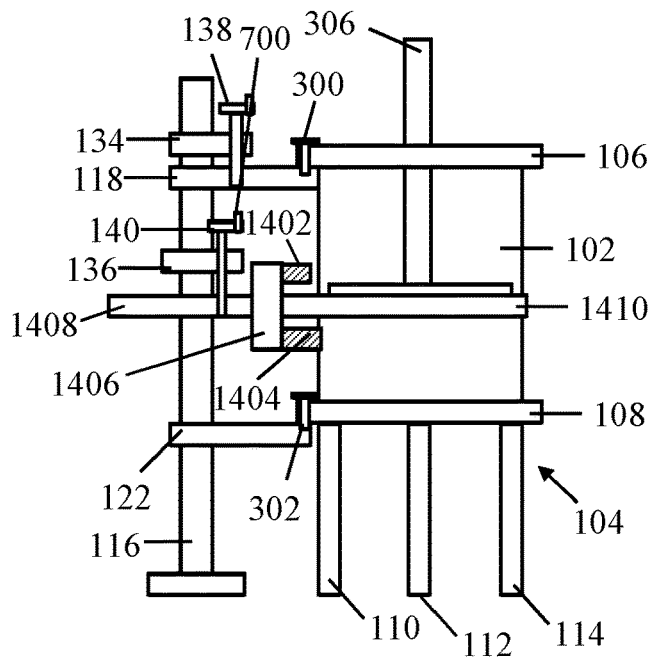
FIGS. 14 and 15 are schematic illustrations of a holding system including pads arranged in an offset configuration in the holding member for holding the chromatography column in accordance to an embodiment.
Figure 15:
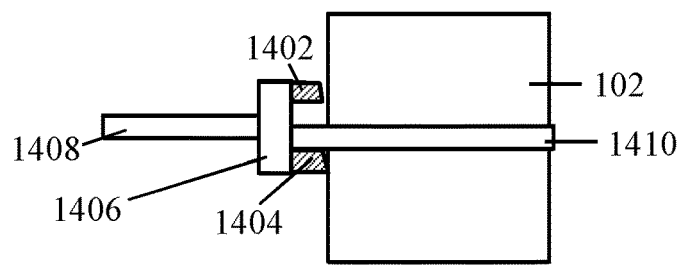
Figure 15:
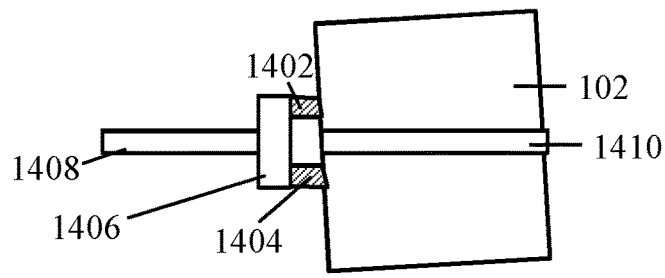

FIG. 14 illustrates a holding system 1400 including pads 1402 and 1404 for holding the chromatography column 102 in accordance with yet another embodiment. The pads 1402 and 1404 may be arranged on a gripping unit 1406 in an offset configuration for holding the chromatography column 102. The pad 1402 (i.e. a first pad) may have a shorter length as compared to the pad 1404 (i.e. a second pad). Thus when in contact with the chromatography column 102 the pad 1404 touches its surface first a holding member 1408 having the gripping unit 1406 is arranged to hold the column 102. Once a clasping member 1410 engaged to the holding member 1408 is wound around the chromatography column 102 tightly, the column 102 tilts so that its surface comes in contact with the pad 1402 as shown in FIG. 15. Consequently, the chromatography column 102 can be tightly held by the holding member 1408 having the gripping unit 1406.

Figure 16:
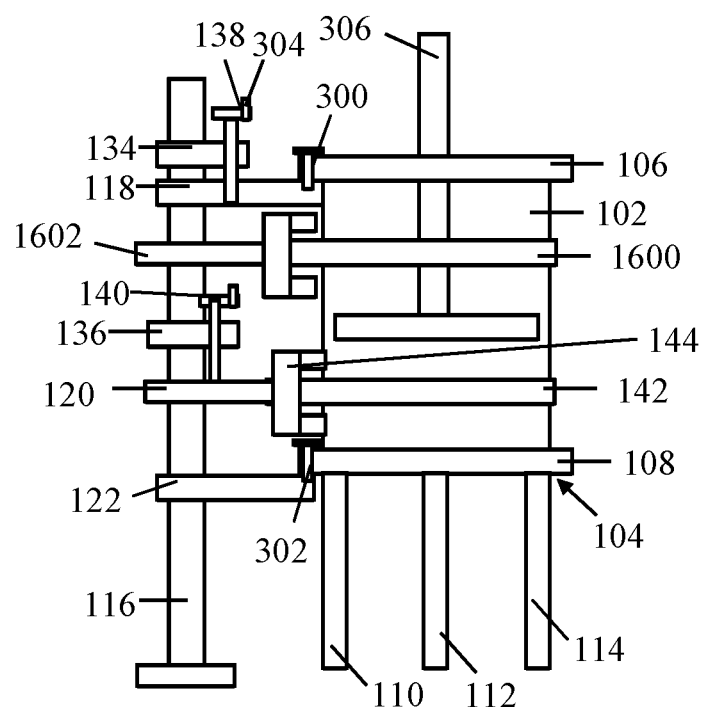
FIG. 16 illustrates a holding system with another clasping member for holding the chromatography column in place in accordance to an embodiment.

FIG. 16 illustrates the holding system 100 with another clasping member 1600 for holding the chromatography column 102 in place in accordance to an embodiment. The holding system 100 includes the holding members 118, 120 and 122 for holding the chromatography column 102 in place on the stand 104. The holding member 120 includes the gripping unit 144 having the pads 800 and 802 arranged along the upright member 116 for holding the chromatography column 102. The clasping member 142 is wound around the chromatography column 102 for holding it. The clasping member 142 is engaged with the holding member 120 as described earlier.

Another clasping member 1600 may be also used to wound around the chromatography column 102. The clasping member 1600 may be disengageably engaged to a holding member 1602 arranged along the upright member 116 so that the chromatography column 102 can be held firmly in position on the stand 104. The second clasping member provides additional grip in holding the chromatography column 102. As described here only two clasping members 142 and 1600 are provided in the holding system 100 however it may be envisioned that more than two clasping members can be arranged along the upright member 116 and additional holding members may be arranged for holding these clasping members in other embodiments.

Figure 17:
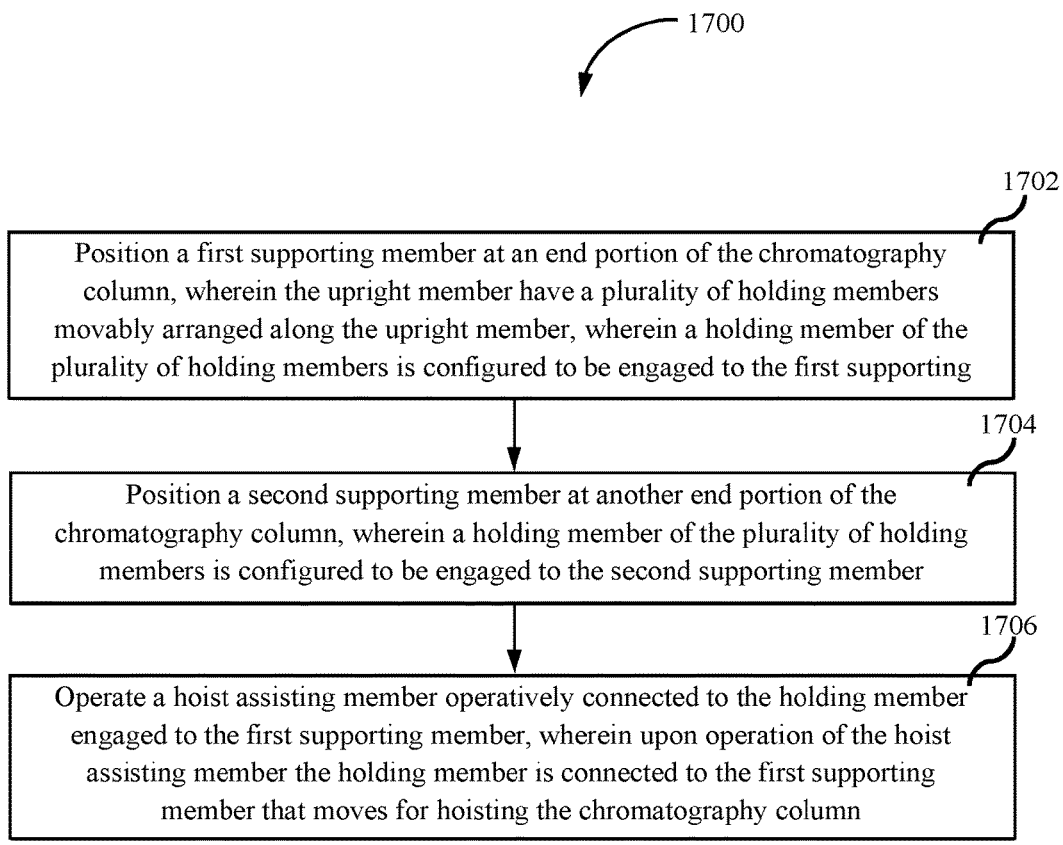
FIG. 17 illustrates a method of holding and hoisting a chromatography column using a holding system according to an embodiment.

FIG. 17 illustrates a method 1700 of holding and hoisting a chromatography column using a holding system according to an embodiment. The chromatography column may be positioned on a chromatography stand. The chromatography stand includes multiple legs for helping to position in an erect fashion. The process of holding and hoisting a chromatography column involves positioning a first supporting member at an end portion of the chromatography column at block 1702. A holding member of the plurality of holding members is configured to be engaged to the first supporting member. The holding members can be arranged at different positions on the upright member based on needs. The first supporting member can also hold an adapter. The adapter may be movably engaged to the first supporting member such that it can be moved up and down. The adapter can be removed after usage from the chromatography column. In order to remove the adapter, the hoist assisting member is tightened to move the holding member closer to the plate member. The first supporting member moves with respect to the plate member thereby the adapter can be lifted out of the chromatography column. Once the adapter is removed the chromatography column can be cleaned. A second supporting member is then positioned at another end portion of the chromatography column at block 1704. The holding member also have a locking slot at one end portion that enables a locking unit to pass through the hole and the locking slot to lock the holding member at the position near the hole or overlapping the hole. Another locking unit may be also present in the holding system. The holes may be circular in configuration however these holes can have different configurations such as square, rectangular, triangular and any parallelogram. Based on the configuration of these holes, a locking slot in a holding member and a locking member may have complementary shape and configuration. In another embodiment the holes may have its internal surface in a threaded configuration so that the locking unit may be a screw like member can pass through the hole. Further it may be appreciated that the disclosed arrangement for arranging the holding members along the upright member is in accordance to an exemplary embodiment and hence it may be envisioned that other constructional arrangements of position locking mechanisms may be possible for arranging the holding members along the upright member. These holding members may have different sizes and shapes based on different requirements.

The holding member of the plurality of holding members is configured to be engaged to the second supporting member. The upright member has multiple holes for enabling fastening members to pass through the upright member to position the first supporting member and the second supporting member on the upright member. This is described in detail in conjunction with FIG. 1. The holding system includes multiple plate members that can be operatively connected to the holding member using hoist assisting members. Thereafter operate a hoist assisting member operatively connected to the holding member engaged to the first supporting member as shown in block 1706. The hoist assisting member is operable to move the holding member connected to the first supporting member for hoisting the chromatography column. In order to hold the chromatography column in a correct position the holding system may be provided with a clasping member that can be connected to the holding member. The clasping member may be wound around the chromatography column. In an embodiment the clasping member may be a belt like member that can be wound around the chromatography column and disengageably engaged to the holding member. The clasping member may include a gripping unit that enables the holding member to be held securely along with the holding force of the clasping member. The holding member along with the gripping unit may have a T-shaped configuration according to an exemplary embodiment. In an embodiment pads are arranged between the gripping unit and the surface of the chromatography column. The pads render more grip onto the surface of the chromatography column. The pads may be fastened on to the surface of the gripping unit. In an embodiment the pads may be stuck on to the gripping unit using a binding material such as a glue material. The pads used may be of different size and shapes. In an embodiment a wedge shaped pad may be used. In another embodiment a pad may include a suction unit. The suction unit may be operated to produce a suction effect for gripping or holding the chromatography column. The suction unit may include a suction pump which when operated produces the suction effect to such air between the pad surface and the surface of the chromatography column. Further the chromatography column can be moved by swinging the clasping member with respect to the upright member. The swinging operation is done only when the adapter is removed from the chromatography column. An additional holding member may be present which will be used for resting the heavy chromatography column after swinging out.

The holding member also have a locking slot at one end portion that enables a locking unit to pass through the hole and the locking slot to lock the holding member at the position near the hole or overlapping the hole. Another locking unit may be also present in the holding system. The holes may be circular in configuration however these holes can have different configurations such as square, rectangular, triangular and any parallelogram. Based on the configuration of these holes, a locking slot in a holding member and a locking member may have complementary shape and configuration. In another embodiment the holes may have its internal surface in a threaded configuration so that the locking unit may be a screw like member can pass through the hole. Further it may be appreciated that the disclosed arrangement for arranging the holding members along the upright member is in accordance to an exemplary embodiment and hence it may be envisioned that other constructional arrangements of position locking mechanisms may be possible for arranging the holding members along the upright member. These holding members may have different sizes and shapes based on different requirements.

From the foregoing, it will appreciate that the above disclosed holding system for holding and hoisting a chromatography column of one or more chromatography columns provide numerous benefits to healthcare enterprises, such as improved way of hoisting and holding adapter used in chromatography columns thereby making the maintenance activity of the chromatography column less labor some for the user. Further as the holding system disclosed here can have numerous holding members which can be re-arranged in different configurations, the holding system can be used for holding and hoisting different size chromatography columns and for performing maintenance activities in these columns. Moreover, the holding system is able to conveniently hoist the chromatography columns and/or any other heavy components thereby rendering it to be safe in handling and precise in its hoisting and holding operations.

This written description uses examples to disclose the invention, including the best mode, and also to enable any person skilled in the art to practice the invention, including making and using any computing system or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

We claim:
1. A holding system for holding and hoisting a chromatography column, the holding system comprising:
an upright member;
a plurality of holding members movably arranged along the upright member;
a first supporting member positioned at an end portion of the chromatography column, wherein a first holding member of the plurality of holding members is configured to be engaged to the first supporting member;
a second supporting member positioned at another end portion of the chromatography column, wherein a third holding member of the plurality of holding members is configured to be engaged to the second supporting member;
a first hoist assisting member operatively connected to the first holding member to move the first holding member connected to the first supporting member for hoisting the chromatography column, and
a second holding member of the plurality of holding members comprises a clasping member disengageably engaged to the second holding member and wound around the chromatography column.
2. The holding system of claim 1, further comprising a second hoist assisting member operatively connected to the second holding member.
3. The holding system of claim 2, further comprising a plurality of plate members, wherein the first hoist assisting member operatively connects a first plate member of the plurality of plate members to the first holding member, which along with the first supporting member moves with respect to the first plate member in response to operation of the first hoist assisting member.
4. The holding system of claim 3, wherein a second plate member of the plurality of plate members is operatively connected to the second holding member using the second hoist assisting member, wherein the second holding member moves with respect to the second plate member in response to operation of the second hoist assisting member.
5. The holding system of claim 1, wherein the second holding member is configured to swing with respect to the upright member for moving the chromatography column.
6. The holding system of claim 1, wherein the second holding member comprises a gripping unit positioned proximal to the chromatography column.
7. The holding system of claim 6, wherein the second holding member comprising the gripping unit has a T-shaped configuration.
8. The holding system of claim 6, wherein the second holding member comprises at least one pad arranged between the gripping unit and a surface of the chromatography column.
9. The holding system of claim 8, wherein the at least one pad has a wedge shape.
10. The holding system of claim 6, wherein the second holding member comprises a first pad and a second pad arranged between the gripping unit and a surface of the chromatography column in an offset configuration, wherein the chromatography column is in a tilted position in response to the second holding member holding the chromatography column.
11. The holding system of claim 1, wherein the first holding member is engaged to the first supporting member using a first fastening member and
the third holding member is engaged to the second supporting member using a second fastening member.
12. The holding system of claim 1, further comprising a locking unit engaging each of the plurality of holding members with the upright member to be positioned on the upright member.
13. A chromatography system comprising
a chromatography column,
a chromatography stand onto which the chromatography column is positioned,
a holding system for holding and hoisting a chromatography column, and
an adapter movable in the chromatography column,
the holding system comprising:
an upright member;
a plurality of holding members movably arranged along the upright member;
a first supporting member positioned at an end portion of the chromatography column, wherein a first holding member of the plurality of holding members is configured to be engaged to the first supporting member, wherein the adapter is operatively connected to the first supporting member for moving in the chromatography column;

a second supporting member comprised in the chromatography stand positioned at another end portion of the chromatography column, with a third holding member of the plurality of holding members configured to be engaged to the second supporting member; and a first hoist assisting member operatively connected to the first holding member to move the first holding member for hoisting the chromatography column and the adapter, wherein a second holding member of the plurality of holding members comprises a clasping member disengageably engaged to the second holding member and wound around the chromatography column.

14. The chromatography system of claim 13, wherein the second holding member is configured to swing with respect to the upright member for moving the chromatography column.

15. The chromatography system of claim 13, further comprising a plurality of plate members, wherein the first hoist assisting member operatively connects a first plate member of the plurality of plate members to the first holding member, which along with the first supporting member moves with respect to the first plate member in response to operation of the first hoist assisting member for hoisting the adapter; and a second plate member of the plurality of plate members operatively connected to the second holding member using a second hoist assisting member, wherein the second holding member moves with respect to the second plate member in response to operation of the second hoist assisting member.

16. The chromatography system of claim 13, wherein the second holding member comprises:

a gripping unit positioned proximal to the chromatography column; and at least one pad arranged between the gripping unit and a surface of the chromatography column.

17. The chromatography system of claim 16, wherein the second holding member comprises a first pad and a second pad arranged between the gripping unit and the surface of the chromatography column in an offset configuration, wherein the chromatography column is in a tilted position in response to the second holding member holding the chromatography column.

18. A method of holding and hoisting a chromatography column using a holding system, the method comprising:

positioning a first supporting member at an end portion of the chromatography column and along an upright member, wherein the upright member comprises a plurality of holding members movably arranged along the upright member, wherein a first holding member of the plurality of holding members is configured to be engaged to the first supporting member;

positioning a second supporting member at another end portion of the chromatography column, wherein a third holding member of the plurality of holding members is configured to be engaged to the second supporting member;

operating a first hoist assisting member operatively connected to the first holding member engaged to the first supporting member, wherein upon operation of the hoist assisting member the first holding member connected to the first supporting member moves for hoisting the chromatography column; and disengageably engaging a clasping member to a second holding member of the plurality of holding members and the clasping member around the chromatography column.

19. The method of claim 18 further comprising:

swinging the second holding member of the plurality of holding members with respect to the upright member for moving the chromatography column.

20. The method of claim 18 further comprising:

operatively connecting a second plate member of a plurality of plate members to the second holding member using a second hoist assisting member, wherein the first holding member along with the first supporting member moves with respect to a first plate member of the pluarity of plate members in response to operation of the first hoist assisting member and the second holding member comprises a gripping unit positioned proximal to the chromatography column, and arranging a pad between the gripping unit and a surface of the chromatography column.

21. The method of claim 20 further comprising engaging each of the holding member with the upright member using a locking unit of a plurality of locking units to be positioned on the upright member.

* * * * *